United States Patent
Ammermann et al.

(10) Patent No.: US 7,074,422 B2
(45) Date of Patent: Jul. 11, 2006

(54) FUNGICIDAL MIXTURES

(75) Inventors: Eberhard Ammermann, Heppenheim (DE); Reinhard Stierl, Freinsheim (DE); Ulrich Schöfl, Brühl (DE); Klaus Schelberger, Gönnheim (DE); Maria Scherer, Godramstein (DE); Michael Henningsen, Frankenthal (DE); Randall Even Gold, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/518,445

(22) PCT Filed: Jun. 30, 2003

(86) PCT No.: PCT/EP03/06892

§ 371 (c)(1),
(2), (4) Date: Dec. 20, 2004

(87) PCT Pub. No.: WO2004/008862

PCT Pub. Date: Jan. 29, 2004

(65) Prior Publication Data

US 2005/0250842 A1  Nov. 10, 2005

(30) Foreign Application Priority Data

Jul. 18, 2002 (DE) .................. 102 32 752

(51) Int. Cl.
*A01P 3/00* (2006.01)
*A01N 47/12* (2006.01)

(52) U.S. Cl. ...................... 424/405; 514/436
(58) Field of Classification Search .............. 424/405
See application file for complete search history.

(56) References Cited

U.S. PATENT DOCUMENTS

| | | | |
|---|---|---|---|
| 3,513,241 A | | 5/1970 | Hoyer et al. |
| 5,650,423 A | * | 7/1997 | Dehne et al. ............ 514/376 |
| 5,910,496 A | * | 6/1999 | Albert et al. ........... 514/237.5 |
| 6,004,570 A | * | 12/1999 | Kostansek .............. 424/407 |
| 6,346,535 B1 | * | 2/2002 | Cotter et al. ............ 514/269 |
| 6,440,440 B1 | * | 8/2002 | Meerpoel et al. ........ 424/405 |
| 6,448,228 B1 | * | 9/2002 | Filippini et al. .......... 514/19 |

FOREIGN PATENT DOCUMENTS

| | | |
|---|---|---|
| DE | 1 567 169 | 8/1970 |
| GB | 857383 | 12/1960 |
| WO | WO-98/26654 A2 | 6/1998 |

OTHER PUBLICATIONS

Colby, WEEDS, Calculating Synergistic and Antagonistic Responses of Herbicide Combinations, vol. 15, pp. 20-22 (1967).

* cited by examiner

*Primary Examiner*—Sabiha Qazi
(74) *Attorney, Agent, or Firm*—Birch, Stewart, Kolasch & Birch, LLP

(57) ABSTRACT

Fungicidal mixtures, comprising
  A) the compound of the formula I and
  B) the compound of the formula II

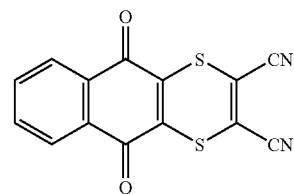

in a synergistically effective amount, methods for controlling harmful fungi using mixtures of the compounds I and II and the use of the compounds I and II for preparing such mixtures are described.

7 Claims, No Drawings

FUNGICIDAL MIXTURES

The present invention relates to fungicidal mixtures, comprising

A) the compound of the formula I

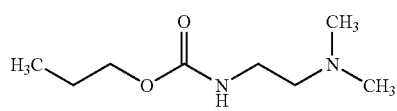

and

B) the compound of the formula II

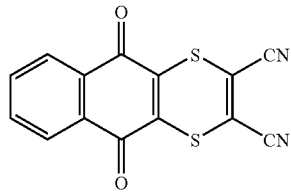

in a synergistically effective amount.

Moreover, the invention relates to methods for controlling harmful fungi using mixtures of the compounds I and II, and to the use of the compounds I and II for preparing such mixtures.

The compound I (propyl (2-dimethylaminoethyl)carbamate; common name: propamocarb], its preparation and its action against harmful fungi are known from the literature [cf. DE-A 15 67 169].

The compound of the formula II (common name: dithianon) and processes for its preparation are described in GB-A 857 383.

The fungicidal activity and in particular the persistence of compound I often leaves something to be desired.

It is an object of the present invention to overcome the disadvantages mentioned and to provide mixtures which have improved action, in particular persistence, against harmful fungi combined with a reduced total amount of active compound applied (synergistic mixtures).

We have found that this object is achieved by the mixtures defined at the outset. Moreover, we have found that applying the compounds I and II simultaneously, either together or separately, or applying the compounds I and II in succession provides better control of harmful fungi than is possible with the individual compounds alone.

When preparing the mixtures, it is preferred to employ the pure active compounds I and II, with which further active compounds against harmful fungi or other pests, such as insects, arachnids or nematodes, or else herbicidal or growth-regulating active compounds or fertilizers can be admixed as required.

The mixtures of the compounds I and II,.or the simultaneous joint or separate use of the compounds I and II, have outstanding action against a wide range of phytopathogenic fungi, in particular from the classes of the Ascomycetes, Deuteromycetes, Oomycetes and Basidiomycetes. Some of them act systemically and are therefore also suitable for use as foliar- and soil-acting fungicides.

They are especially important for controlling a large number of fungi in a variety of crop plants, such as cotton, vegetable species (for example cucumbers, beans and cucurbits), fruit species, grapevine, wheat, ornamentals, sugarcane and a variety of seeds.

They are particularly suitable for controlling the following phytopathogenic fungi: *Erysiphe cichoracearum* and *Sphaerotheca fuliginea* in cucurbits, *Podosphaera leucotricha* in apples, *Uncinula necator* in grapevines, *Venturia inaequalis* (scab) in apples, *Septoria tritici* in wheat, *Botrytis cinerea* (gray mold) in strawberries, vegetables, ornamentals and grapevines, *Cercospora arachidicola* in groundnuts, *Phytophthora infestans* in potatoes and tomatoes, *Pseudoperonospora* species in cucurbits and hops, *Plasmopara viticola* in grapevines, *Alternaria* species in vegetables and fruit and *Fusarium* and *Verticillium* species.

The compounds I and II can be applied simultaneously, either together or separately, or in succession, the sequence, in the case of separate application, generally not having any effect on the control results.

The compounds I and II are usually applied in a weight ratio of from 1:100 to 10:1, preferably from 1:10 to 5:1, in particular from 5:1 to 1:5.

Depending on the nature of the desired effect, the application rates of the mixtures according to the invention are, for the compounds I, from 5 g/ha to 500 g/ha, preferably from 50 to 500 g/ha, in particular from 50 to 200 g/ha.

Correspondingly, the application rates of the compound II are generally from 5 to 2000 g/ha, preferably from 10 to 1000 g/ha, in particular from 50 to 750 g/ha.

For seed treatment, the application rates of the mixture are generally from 0.001 to 1 g/kg of seed, preferably from 0.01 to 0.5 g/kg, in particular from 0.01 to 0.1 g/kg.

If phytopathogenic harmful fungi are to be controlled, the separate or joint application of the compounds I and II or of the mixtures of the compounds I and II is effected by spraying or dusting the seeds, the plants or the soils before or after sowing, or before or after plant emergence.

The fungicidal synergistic mixtures according to the invention, or the compounds I and II, can be formulated, for example, in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform a distribution as possible of the mixture according to the invention.

The formulations are prepared in a manner known per se, for example by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, for example ligno-, phenol-, naphthalene- and dibutylnaphthalenesulfonic acids, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl-, or nonylphenol, alkylphenyl polyglycol ethers, tributylphenyl polyglycol ethers, alkylaryl polyether alcohols, triisodecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methyl cellulose.

Powders, materials for broadcasting and dusts can be prepared by mixing or jointly grinding the compounds I and II or the mixture of the compounds I and II with a solid carrier.

Granules (for example coated granules, impregnated granules or homogeneous granules) are usually prepared by binding the active compound, or active compounds, to a solid carrier.

Fillers or solid carriers are, for example, mineral earths, such as silica gel, silicic acids, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of one of the compounds I and II or of the mixture of the compounds I and II. The active compounds are employed in a purity of from 90% to 100%, preferably from 95% to 100% (according to NMR spectrum or HPLC).

The compounds I and II, the mixtures or the corresponding formulations are applied by treating the harmful fungi, the plants, seeds, soils, areas, materials or spaces to be kept free from them with a fungicidal effective amount of the mixture, or of the compounds I and II in the case of separate application. Application can be effected before or after infection by the harmful fungi.

Examples of such preparations comprising the active compounds are:

I. a solution of 90 parts by weight of the active compounds and 10 parts by weight of N-methylpyrrolidone; this solution is suitable for use in the form of microdrops;

II. a mixture of 20 parts by weight of the active compounds, 80 parts by weight of xylene, 10 parts by weight of the adduct of 8 to 10 mol of ethylene oxide to 1 mol of oleic acid N-monoethanolamide, 5 parts by weight of the calcium salt of dodecylbenzenesulfonic acid, 5 parts by weight of the adduct of 40 mol of ethylene oxide and 1 mol of castor oil; a dispersion is obtained by finely distributing the solution in water;

III. an aqueous dispersion of 20 parts by weight of the active compounds, 40 parts by weight of cyclohexanone, 30 parts by weight of isobutanol, 20 parts by weight of the adduct of 40 mol of ethylene oxide and 1 mol of castor oil;

IV. an aqueous dispersion of 20 parts by weight of the active compounds, 25 parts by weight of cyclohexanol, 65 parts by weight of a mineral oil fraction of boiling point 210 to 280° C., and 10 parts by weight of the adduct of 40 mol of ethylene oxide and 1 mol of castor oil;

V. a mixture, ground in a hammer mill, of 80 parts by weight of the active compounds, 3 parts by weight of the sodium salt of diisobutylnaphthalene-1-sulfonic acid, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of the active compounds and 97 parts by weight of finely divided kaolin; this dust comprises 3% by weight of active compound;

VII. an intimate mixture of 30 parts by weight of the active compounds, 92 parts by weight of pulverulent silica gel and 8 parts by weight of paraffin oil which had been sprayed onto the surface of this silica gel; this formulation imparts good adhesion to the active compound;

VIII. a stable aqueous dispersion of 40 parts by weight of the active compounds, 10 parts by weight of the sodium salt of a phenolsulfonic acid/urea/formaldehyde condensate, 2 parts by weight of silica gel and 48 parts by weight of water; this dispersion may be diluted further;

IX. a stable oily dispersion of 20 parts by weight of the active compounds, 2 parts by weight of the calcium salt of dodecylbenzenesulfonic acid, 8 parts by weight of fatty alcohol polyglycol ether, 20 parts by weight of the sodium salt of a phenolsulfonic acid/urea/formaldehyde condensate and 88 parts by weight of a paraffinic mineral oil.

The fungicidal activity of the compound and of the mixtures can be demonstrated by the following experiments:

The active compounds were prepared separately or together as a stock solution comprising 0.25% of active compound in acetone or DMSO. 1% by weight of the emulsifier Uniperol® EM (wetting agent having emulsifying and dispersing action based on ethoxylated alkylphenols) was added, and the mixture was diluted with water to the desired concentration.

Evaluation is carried out by determining the infected leaf areas in percent. These percentages are converted into efficacies. The expected efficacies of the active compound mixtures are determined using Colby's formula [R. S. Colby, Weeds 15, 20-22 (1967)] and compared with the observed efficacies.

Colby's formula:

$$E=x+y-x.y/100$$

E expected efficacy, expressed in % of the untreated control, when using the mixture of the active compounds A and B at the concentrations a and b x efficacy, expressed in % of the untreated control, when using active compound A at a concentration of a y efficacy, expressed in % of the untreated control, when using active compound B at a concentration of b The efficacy (E) is calculated as follows using Abbot's formula:

$$E=(1-\alpha/\beta)\cdot 100$$

$\alpha$ corresponds to the fungal infection of the treated plants in % and $\beta$ corresponds to the fungal infection of the untreated (control) plants in %

An efficacy of 0 means that the infection level of the treated plants corresponds to that of the untreated control plants; an efficacy of 100 means that the treated plants were not infected.

EXAMPLE

Activity Against Peronospora of Vines Caused by *Plasmopara viticola*

Leaves of potted vines of the cultivar "Müller-Thurgau" were sprayed to runoff point with an aqueous suspension having the concentration of active compound stated below. To be able to assess the persistence of the substances, the plants were, after the spray coating had dried on, placed in a green house for 3 days. Only then were the leaves inoculated with an aqueous zoospore suspension of *Plasmopara viticola*. The vines were then initially placed in a water-vapor-saturated chamber at 24° C. for 48 hours and then in a greenhouse at 20-30° C. for 5 days. After this period of time, the plants were again placed in a moist chamber for 16 hours to promote sporangiophore eruption. The extent to which the infection had developed on the undersides of the leaves was then determined visually.

TABLE A

Individual active compounds

| Example | Active compound | Concentration of active compound in the spray liquor [ppm] | Efficacy in % of the untreated control |
|---|---|---|---|
| 1 | control (untreated) | (88% infection) | 0 |
| 2 | I propamocarb | 30 | 0 |
|   |   | 15 | 0 |
|   |   | 7.5 | 0 |
|   |   | 3.75 | 0 |
| 3 | II dithianon | 30 | 89 |
|   |   | 15 | 32 |
|   |   | 7.5 | 20 |
|   |   | 3.75 | 0 |

TABLE B

Combinations according to the invention

| Example | Active compound mixture Concentration Mixing ratio | Observed efficacy | Calculated efficacy* |
|---|---|---|---|
| 4 | I + II 30 + 30 ppm 1:1 | 100 | 89 |
| 5 | I + II 15 + 15 ppm 1:1 | 100 | 32 |
| 6 | I + II 3.75 + 3.75 ppm 1:1 | 94 | 0 |
| 7 | I + II 3.75 + 15 ppm 1:4 | 92 | 32 |
| 8 | I + II 30 + 7.5 ppm 4:1 | 99 | 20 |
| 9 | I + II 15 + 3.75 ppm 4:1 | 54 | 0 |

*)efficacy calculated using Colby's formula

The test results show that, for all mixing ratios, the observed efficacy is higher than the efficacy predicted using Colby's formula.

We claim:
1. A fungicide mixture, comprising
A) the compound of the formula I

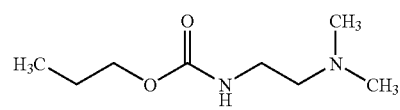

I and
B) the compound of the formula II

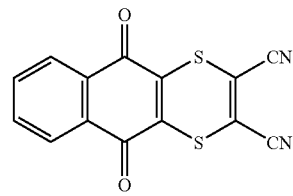

II in a synergistically effective amount.

2. A fungicidal mixture as claimed in claim 1, wherein the weight ratio of the compound I to the compound II is from 10:1 to 1:100.

3. A fungicidal mixture comprising a solid or liquid carrier and a mixture as claimed in claim 1.

4. A method for controlling harmful fungi, which comprises treating the harmful fungi, their habitat, or the plants, seeds, soils, areas, materials or spaces to be kept free from them, with the compound of the formula I and the compound of the formula II as set forth in claim 1.

5. A method as claimed in claim 4, which comprises treating the harmful fungi, their habitat or the plants, seeds, soils, areas, materials or spaces to be kept free from them with from 5 to 500 g/ha of the compound I as set forth in claim 1.

6. A method as claimed in claim 4, which comprises treating the harmful fungi, their habitat or the plants, seeds, soils, areas, materials or spaces to be kept free from them with from 5 to 2000 g/ha of the compound II as set forth in claim 1.

7. A method of preparing a fungicide mixture, comprising:
mixing the compound of the formula I and the compound of the formula II as set forth in claim 1.

* * * * *